United States Patent
Parise et al.

(10) Patent No.: US 10,303,923 B1
(45) Date of Patent: May 28, 2019

(54) QUANTITATION OF NETOSIS USING IMAGE ANALYSIS

(71) Applicants: The University of North Carolina at Chapel Hill, Chapel Hill, NC (US); The University of South Carolina, Columbia, SC (US)

(72) Inventors: Leslie Victoria Parise, Chapel Hill, NC (US); Noah Sciaky, Chapel Hill, NC (US); Laila Elsherif, Chapel Hill, NC (US); Joshua Nathan Cooper, Columbia, SC (US)

(73) Assignees: The University of North Carolina at Chapel Hill, Chapel Hill, NC (US); The University of South Carolina, Columbia, SC (US)

( * ) Notice: Subject to any disclaimer, the term of this patent is extended or adjusted under 35 U.S.C. 154(b) by 0 days.

(21) Appl. No.: 16/031,762

(22) Filed: Jul. 10, 2018

(51) Int. Cl.
| | |
|---|---|
| *G06K 9/00* | (2006.01) |
| *G01N 1/30* | (2006.01) |
| *G06T 7/00* | (2017.01) |
| *G06T 3/40* | (2006.01) |
| *G06K 9/62* | (2006.01) |

(52) U.S. Cl.
CPC .......... *G06K 9/00147* (2013.01); *G01N 1/30* (2013.01); *G06K 9/0014* (2013.01); *G06K 9/6261* (2013.01); *G06T 3/4038* (2013.01); *G06T 7/0012* (2013.01); *G06K 2209/05* (2013.01); *G06T 2207/10056* (2013.01); *G06T 2207/20081* (2013.01); *G06T 2207/20084* (2013.01); *G06T 2207/30024* (2013.01); *G06T 2207/30242* (2013.01)

(58) Field of Classification Search
None
See application file for complete search history.

(56) References Cited

U.S. PATENT DOCUMENTS

| | | | |
|---|---|---|---|
| 9,739,783 B1* | 8/2017 | Kumar | G01N 33/57492 |
| 2013/0101996 A1* | 4/2013 | Kono | G01N 15/1468 |
| | | | 435/6.1 |
| 2015/0104467 A1* | 4/2015 | Constantin | C07K 16/28 |
| | | | 424/173.1 |
| 2016/0061824 A1* | 3/2016 | Hahn | G01N 33/5308 |
| | | | 436/501 |

(Continued)

OTHER PUBLICATIONS

Barr et al., "Deterministic Walks with Choice," Discrete Applied Mathematics, vol. 162, pp. 100-107 (2014).

(Continued)

*Primary Examiner* — Delomia L Gilliard
(74) *Attorney, Agent, or Firm* — Jenkins, Wilson, Taylor & Hunt, P.A.

(57) ABSTRACT

Methods and systems for characterization of NETosis (Neutrophil Extracellular Traps) in neutrophils. In some examples, a method includes acquiring an image of a sample of neutrophils. The method includes classifying each neutrophil depicted in the image as having either a NETotic or non-NETotic nucleus using one or more processors executing a convolutional neural network (CNN) trained on training images of NETotic and non-NETotic neutrophil nuclei. The method includes generating output indicative of a number of neutrophils classified as having a NETotic nucleus and a number of neutrophil classified as having a non-NETotic nucleus.

20 Claims, 8 Drawing Sheets

(56) References Cited

U.S. PATENT DOCUMENTS

| | | | |
|---|---|---|---|
| 2017/0076448 A1* | 3/2017 | Chen | G06T 7/0012 |
| 2018/0057574 A1* | 3/2018 | Nakazawa | C07K 16/241 |

OTHER PUBLICATIONS

Barrientos et al., "An Improved Strategy to Recover Large Fragments of Functional Human Neutrophil Extracellular Traps," Frontiers in Immunology, vol. 4, Article 168, pp. 1-10 (Jun. 2013).

Barry et al., "Molecular Basis of CIB Binding to the Integrin αIIb Cytoplasmic Domain," The Journal of Biological Chemistry, vol. 277, No. 32, pp. 28877-28883 (May 21, 2002).

Bennewitz et al., "Lung vaso-occulation in sickle cell disease mediated by arteriolar neutrophil-platelet microemboli," JCI Insight, vol. 2, No. 1, pp. 1-19 (Jan. 12, 2017).

Bianchi et al., "Restoration of NET formation by gene therapy in CGD controls aspergillosis," Blood, vol. 114, No. 13, pp. 2619-2622 (Sep. 2009).

Black et al., "CIB1 depletion impairs cell survival and tumor growth in triple-negative breast cancer," Breast Cancer Res Treat., vol. 152, No. 2, pp. 1-16 (Jul. 2015).

Borikova et al., "Rho Kinase Inhibition Rescues the Endothelial Cell Cerebral Cavernous Malformation Phenotype," Journal of Biological Chemistry, vol. 285, No. 16, pp. 11760-11764 (Apr. 16, 2010).

Bouchard et al., "Platelets do not express the oxidized or reduced forms of tissue factor," Biochim Biophys Acta., vol. 1840, No. 3, pp. 1-16 (Mar. 2014).

Brinkmann et al., "Automatic quantification of in vitro NET formation," Frontiers in Immunology, vol. 3, Article 413, pp. 1-8 (Jan. 2013).

Brinkmann et al., "Neutrophil Extracellular Traps Kill Bacteria," Science, vol. 303, pp. 1532-1535 (Mar. 5, 2004).

Brittain et al., "Activation of Sickle Red Blood Cell Adhesion via Integrin-Associated Protein/CD47-Induced Signal Transduction," The Journal of Clinicals Investigation, vol. 107, No. 12, pp. 1555-1562 (Jun. 2001).

Brittain et al., "Fibronectin bridges monocytes and reticulocytes via integrin α4β1," British Journal of Haematology, vol. 141, pp. 872-881 (Apr. 18, 2008).

Brummel-Ziedins et al., "Activated protein C inhibitor for correction of thrombin generation in hemophilia A blood and plasma1," Journal of Thrombosis and Haemostasis, vol. 9, pp. 2262-2267 (Sep. 6, 2011).

Brummel-Ziedins et al., "The Resuscitative Fluid You Choose May Potentiate Bleeding," The Journal of TRAUMA® Injury, Infection, and Critical Care, vol. 61, No. 6, pp. 1350-1358 (Dec. 2006).

Brummel-Ziedins et al., "Thrombin generation and bleedig in hemophilia A," Haemophilia., vol. 15, No. 5, pp. 1-11 (Sep. 2009).

Chai et al., "Assay Validation in High Throughput Screening—from Concept to Application," Drug Discovery and Development—From Molecules to Medicine, InTech, http://www.intechopen.com/books/drug-discovery-and-development-from-molecules-tomedicine/assay-validation-in-high-throughput-screening-from-concept-to-application, pp. 221-239 (2015).

Chang et al., "Analytic Connectivity of k-uniform hypergraphs," http://arxiv.org/abs/1507.02763, pp. 1-15 (Jun. 10, 2015).

Chantrathammachart et al., "Tissue Factor Promotes Activation of Coagulation and Inflammation in a Mouse Model of Sickle Cell Disease," Blood, vol. 120, No. 3, pp. 636-646 (Jul. 19, 2012).

Chen et al., "Heme-induced neutrophil extracellular traps contribute to the pathogenesis of sickle cell disease," Blood, vol. 123, No. 24, pp. 3818-3827 (2014).

Chen et al., "Release and activity of histone in diseases, " Cell Death and Disease, vol. 5, pp. 1-9 (Aug. 14, 2014).

Chow et al., "Statins Enhance Formation of Phagocyte Extracellular Traps," Cell Host Microbe., vol. 8, No. 5, pp. 1-20 (Nov. 18. 2010).

Cichy et al., "Comparison of deep neural networks to spatio-temporal cortical dynamics of human visual object recognition reveals hierarchial correspondance," Scientific Reports, vol. 6, pp. 1-13 (2016).

Ciresan et al., "Deep Neural Networks Segment Neuronal Membranes in Electron Microscopy Images," Advances in Neural Information Processing Systems, vol. 25, pp. 2843-2851 (2012).

Ciresan et al., "Mitosis Detection in Breast Cancer Histology Images with Deep Neural Networks," Proc. Med Image Comput Comput Assist Interv, vol. 16, No. 2, pp. 411-418 (2013).

Clark et al., "Platelet TLR4 activates neutrophil extracellular traps to ensnare bacteria in septic blood," Nat. Med., vol. 13, No. 4, pp. 463-469 (Apr. 2007).

Coelho et al., "Automatic determination of NET (neutrophil extracellular traps) coverage in fluorescent microscopy images," Bioinformatics, vol. 31, No. 14, pp. 2364-2370 (2015).

Cooper, "A Permutation Regulatiry Lemma," The Electronic Journal of Combinations, vol. 13, #R22 (2006).

Cooper et al., "Computing Hypermatrix Spectra eith the Poisson Product Formula," Linear and Multilinear Alg., pp. 1-14 (Jan. 19, 2013).

Cooper et al., "Deterministic Random Walks on Regular Trees," Random Structures & Algorithms, vol. 37, No. 3, pp. 353-366 (2010).

Cooper et al., "Linearly Bounded Liars, Adaptive Covering Codes, and Deterministic Random Walks," J. Combinatorics Special Issue Dedicated to Joel Spencer, pp. 1-23 (Aug. 31, 2009).

Cooper, "Quasirandom Arithmetic Permutations," Journal of Number Theory, vol. 114, No. 1, pp. 1-19 (2005).

Cooper, "Quasirandom Permutations," Journal of Combinatorial Theory, Series A, vol. 106, No. 1, pp. 123-142 (2004).

Cooper et al., "Simulating a Random Walk with Constant Error," Combinatorics, Probability, and Computing, vol. 15, No. 06, pp. 815-822 (2006).

Cooper et al., "Spectra of uniform hypergraphs," Linear Algebra and its Applications, vol. 436, No. 9, pp. 3268-3292 (2012).

Crose et al., "Cerebral Cavernous Malformation 2 Protein Promotes Smad Ubiquitin Regulatory Factor 1-mediated RhoA Degradations in Endothelial Cells," J Biol Chem, vol. 284, No. 20, pp. 13301-13305 (May 15, 2009).

DeNofrio et al., "Characterization of calcium- and integrin-binding protein (CIB1) knockout platelets: potential compensation by CIB family members," J Thromb Haem, vol. 100, No. 5, pp. 1-21 (2008).

Douda et al., "SK3 channel and mitochrondrial ROS mediate NADPH oxidase-independent NETosis induced by calcium influx," PNAS, vol. 112, No. 9, pp. 2817-2822 (Mar. 3, 2015).

Elsherif et al., "Quantitation of Suicidal NETosis Using Convolutional Neural Networks in Human Neutrophils," University of North Carolina-Chapel Hill & University of South Carolina-Columbia, pp. 1 (2016).

Elsherif et al., "Combined Deficiency of Dystrophin and β1 Integrin in the Cardiac Myocyte Causes Myocardial Dysfunction, Fibrosis and Calcification," Circulation Research, vol. 102, No. 9, pp. 1109-1117 (2008).

Elsherif et al., "Dietary copper restriction-induced changes in myocardial gene expression and the effects of copper repletion," Exp Biol Med, vol. 229, pp. 616-622 (2004).

Elsheirif et al., "Regression of copper restriction-induced cardiomyopathy by copper repletion in mice," J Nutr, vol. 134, No. 4, pp. 855-860 (2004).

Evans et al., "Impairment of neutrophil oxidative burst in children with sickle cell disease is associated with heme oxygenase-1," Haematologica, vol. 100, No. 12, pp. 1508-1516 (2015).

Freeman et al., "Identification of novel integrin binding partners for CIB1: structural and thermodynamic basis of CIB1 promisuity," Biochemistry, vol. 52, No. 40, pp. 1-18 (2013).

Fuchs et al., "Extracellular DNA traps promote thrombosis," Proc. Natl. Acad. Sci., vol. 107, No. 36, pp. 15880-15885 (Sep. 7, 2010).

Fuchs et al., "Novel cell death program leads to neutrophil extracellular traps," J Cell Biol, vol. 176, No. 2, pp. 231-241 (Jan. 15, 2007).

Gama et al., "PARC/CUL9 Mediated the Degradation of Mitochondrial-released Cytochrome c and Promotes Survival in Neurons and Cancer Cells," Sci Signal., vol. 7, No. 334 (Jul. 15, 2014).

(56) References Cited

OTHER PUBLICATIONS

Garcia-Romo et al., "Netting neutrophils are major inducers of type I IFN production in pediatric systemic lupus erythematosus," Sci Transl Med., vol. 3, No. 73, pp. 1-20 (Mar. 9, 2011).
Gavillet et al., "Flow Cytometric Assay for Direct Quantification of Neurophil Extracellular Traps in Blood Samples," American Journal of Hematology, vol. 90, No. 12, pp. 1-9 (Dec. 2015).
Geddings et al., "Tissue Factor-Positive Tumor Microvesicles Activate Platelets and Enhance Thrombosis in Mice," J Thromb Haemost., vol. 14, No. 1, pp. 1-26 (Jan. 2016).
Gentry et al., "Structural and Biochemical Characterization of CIB1 Delineates a New Family of EF-hand-containing proteins," J Biol Chem., vol. 280, No. 9, pp. 8407-8415 (2005).
Gissel et al., "The influence of prophylactic factor VIII in severe haemophilia A," Haemophilia, vol. 18, No1. 2, pp. 1-15 (Mar. 2012).
Guimaraes-Costa et al., "Leishmania amazonensis promastigotes induce and are killed by neutrophil extaracellular traps," Proc Natl Acad Sci, vol. 106, No. 16, pp. 6748-6753 (Apr. 21, 2009).
Hakkim et al., "Activation of the Raf-MEK-ERK pathway is required for neutrophil extracellular trap formation," Nat Chem Biol., vol. 7, pp. 75-77 (Feb. 2011).
Hines et al., "Novel epinephrine and cyclic AMP-mediated activation of BCAM/Lu-dependent sickle (SS) RBC adhesion," Blood, vol. 101, No. 8, pp. 3281-3287 (Apr. 15, 2003).
Hoffman et al., "Interindividual variation of NETosis in healthy donors: introduction and application of a refined method for extracellular trap quantification," Experimental Dermatology, vol. 25, pp. 895-900 (2016).
Holly et al., "Chemoproteomic Discovery of AADACL1 as a Novel Regulator of Human Platelet Activation," Chemistry and Biology, vol. 20, No. 9, pp. 1125-1134 (Sep. 19, 2013).
Huang et al., "Topoisomerase inhibitors unsilence the dormant allele of Ube3a in neurons," Nature, vol. 481, No. 7380, pp. 185-189 (Dec. 21, 2011).
Jordan et al., "SWI/SNF Chromatin-Remodeling Factor Smarcd3/Baf60c Controls Epithelial-Mesenchymal Transition by Inducing Wnt5a Signaling," Molecular and Cellular Biology., vol. 33, No. 15, pp. 3011-3025 (Aug. 2013).
Kraaij et al., "A novel method for high-throughput detection and quantification of neutrophil extracellular traps reveals ROS-independent NET release with immune complexes," Autoimmunity Reviews, vol. 15, No. 6, pp. 577-584 (2016).
Kroeze et al., "Presto-Tango: an open-source resource for interrogation of the druggable human GPCR-ome," Nat Struct Mol Biol., vol. 22, No. 5, pp. 362-369 (May 2015).
Lande et al., "Neutrophils Activate Plasmacytoid Dendritic Cells by Releasing Self-DNA-Peptide Complexes in Systemic Lupus Erythematosus," Sci. Transl. Med., vol. 3, No. 73, pp. 1-20 (Mar. 9, 2011).
Lee et al., "Phase I Study of Eptifibatide in Patients with Sickle Cell Anaemia," Br J Haem, vol. 139, pp. 612-620 (2007).
Leisner et al., "CIB1: A small protein with big ambitions," FASEB J, vol. 30, pp. 2640-2650 (Aug. 2016).
Leisner et al., "CIB1 prevents nuclear GAPDH accumulation and non-apoptotic tumor cell death via AKT and ERK signaling," Oncogene, vol. 32, No. 34, pp. 4017-4027 (Aug. 22, 2013).
Leisner et al., "Essential role of CIB1 in regulating PAK1 activation and cell migration," J Cell Biol., vol. 170, No. 3, pp. 465-476 (Aug. 1, 2005).
Li et al., "PAD4 is essential for antibacterial innate immunity mediated by neutrophil extracellular traps," The Journal of Experimental Medicine, vol. 207, No. 9, pp. 1853-1862 (2010).
Litjens et al., "Deep learning as a tool for increased accuracy and efficiency of histopathological diagnosis,"Scientific Repots, vol. 6, 26286, pp. 1-11 (2016).
Malone et al., "Laser-scanning velocimetry: A confocal microscopy method for quantitative measurement of cardiovascular performance in zebrafish embryos and larvae," BMC Biotechnol., vol. 7, No. 40, pp. 1-11 (Jul. 10, 2007).

Manda-Handzlik et al., "Flow cytometric quantification of neutrophil extracellular traps: Limitations of the methodological approach," Am. J. Hematol., vol. 91, No. 3, pp. E9-E10 (Mar. 2016).
Mann et al., "Citrate anticoagulation and the dynamics of thrombin generation," J Thromb Haemost., vol. 5, No. 10, pp. 2055-2061 (2007).
Manso et al., "Integrins, membrane-type matrix metalloproteinases and ADAMs: Potential implications for cardiac remodeling," Cardiovasc Res, vol. 69, No. 3, pp. 574-584 (2006).
Masuda et al., "NETosis markers: Quest for specific, objective, and quantitative markers," Clin Chim Acta., vol. 459, pp. 89-93 (2016).
Metzler et al., "Myeloperoxidase is required for neutrophil extracellular trap formation: implications for innate immunity," Blood, vol. 117, No. 3, pp. 953-959 (Jan. 20, 2011).
Mollapour et al., "Raised Neutrophil Phospholipase A2 Activity and Defective Priming of NADPH Oxidase and Phospholipase A2 in Sickle Cell Disease," Blood, vol. 91, No. 9, pp. 3423-3429 (1998).
Monks et al., "Three Dimensional Segregation of Supramolecular Activation Clusters in T Cells," Nature, vol. 395, No. 6697, pp. 82-86 (Sep. 3, 1998).
Morshed et al., "NADPH Oxidase-Independent Formation of Extracellular DNA Traps by Basophils," J Immunol., vol. 192, pp. 5314-5323 (2014).
Naik et al., "Identification of a Novel Calcium-Binding Protein That Interacts with the Integrin αIIb Cytoplasmic Domain," J Biol Chem, vol. 272, No. 8, pp. 4651-4654 (1997).
Nakazawa et al., "Enhanced Formation and Disordered Regulation of NETs in Myeloperoxidase-ANCA-Associated Microscopic Polyangiitis," J Am Soc Nephrol, vol. 25, No. 5, pp. 990-997 (2014).
Neeli et al., "Opposition between PKC isoforms regulates histone deimination and neutrophil extracellular chromatin release," Frontiers in Immunol., vol. 4, Article 38, pp. 1-9 (Feb. 2013).
Ning et al., "Toward Automatic Phenotyping of Developing Embryos from Videos," IEEE Transactions on Image Processing, vol. 14, pp. 1360-1371 (2005).
Parker et al., "Requirements for NADPH oxidase and myeloperoxidase in neutrophil extracellular trap formation differ depending on the stimulus," J. Leukoc. Biol., vol. 92, pp. 841-849 (Oct. 2012).
Papayannopoulos et al., "Neutrophil elastase and myeloperoxidase regulate the formation of neutrophil extracellular traps," J. Cell Biol., vol. 191, No. 3, pp. 677-691 (2010).
Pillai et al., "Mx1 reveals innate pathways to antiviral resistance and lethal influenza disease," Science, vol. 352, pp. 463-466 (2016).
Pilsczek et al., "A Novel Mechanism of Rapid Nuclear Neutrophil Extracellular Trap Formation in Response to *Staphylococcus aureus*," J Immunol., vol. 185, pp. 7413-7425 (2010).
Poirier et al., "Antimicrobial histones and DNA traps in invertebrate immunity: evidences in Crassostrea gigas," J Biol Chem., vol. 289, Nom 36, pp. 24821-24831 (Sep. 5, 2014).
Qari et al., "Flow cytometric assessment of leukocyte function in sickle cell anemia," Hemoglobin, vol. 35, pp. 367-381 (2011).
Riazuddin et al., "Mutations of CIB2, a calcium and integrin binding protein, cause Usher syndrome type 1J and nonsyndromic deafness DFNB48," Nature Genetics, vol. 44, No. 11, pp. 1265-1271 (2012).
Robb et al., "Invertebrate extracellular phagocyte traps show that chromatin is an ancient defence weapon," Nat Comm., vol. 5, pp. 1-11 (2014).
Sciaky et al., "Golgi Tubule Traffic and the Effects of Brefeldin A Visualized in Living Cells," Journal of Cell Biology, vol. 139, No. 5, pp. 1137-1155 (1997).
Selvaraju et al., "Grad-CAM: Visual Explanations from Deep Networks via Gradient-based Localization," pp. 1-24 (Mar. 21, 2017).
Shintani, "Isolation of Neutrophils/Assay of O2- (Superoxide Anion Radical) Generation by Cytochrome-C Reduction," Pharm Anal Acta., vol. 4, No. 6, pp. 1-2 (2013).
Simonyan et al., "Very Deep Convolutional Networks for Large-Scale Image Recognition," pp. 1-14 (Sep. 2014).
Sohn, "NETosis in Autoimmune disease," J Rheum Dis., vol. 23, No. 2, pp. 82-87 (2016).

(56) References Cited

OTHER PUBLICATIONS

Stoiber et al., "The Role of Reactive Oxygen Species (ROS) in the Formulation of Extracellular Traps (ETs) in Humans," Biomolecules, vol. 5, No. 2, pp. 702-723 (2015).
Stuhlmiller et al., "Inhibition of Lapatinib-Induced Kinome Reprogramming in ERBB2-Positive Breast Cancer by Targeting BET Family Bromodomains," Cell Reports, vol. 11, No. 3, pp. 390-404 (Apr. 21, 2015).
Tripette et al., "Red blood cell aggregation, aggregate strength and oxygen transport potential of blood are abnormal in both homozygous sickle cell anemia and sickle-hemoglobin C disease," Haematologica, vol. 94, No. 8, pp. 1060-1065 (2009).
Urban et al., "Neutrophil extracellular traps capture and kill Candida albicans yeast and hyphal forms," Cell. Microbiol., vol. 8, No. 4, pp. 668-676 (2006).
Van Avondt et al., "Ligation of Signal Inhibitory Receptor on Leukocytes-1 Suppresses the Release of Neutrophil Extracellular Traps in Systemic Lupus Erythematosus," PLOS One, vol. 8, Issue 10, pp. 1-9 (Oct. 2013).
Van der Linden et al., "Differential Signalling and Kinetics of Neutrophil Extracellular Trap Release Revealed by Quantitative Live Imaging," Sci Rep, vol. 7, pp. 1-11 (2017).
Von Kšckritz-Blickwede et al., "Phagocytosis-independent antimicrobial activity of mast cells by means of extracellular trap formation," Blood, vol. 111, pp. 3070-3080 (2008).
Wang et al., "Cardiac Metallothionein Induction Plays the Major Role in the Prevention of Diabetic Cardiomyopathy by Zinc Supplementation," Circulation, vol. 113, No. 4, pp. 544-554 (2006).
Wang et al., "Histone hypercitrullination mediates chromatin decondensation and neutrophil extracellular trap formation," J Cell Biol, vol. 184, pp. 205-213 (2009).
Wang et al., "Rap1b is critical for glycoprotein VI-mediated but not ADP receptor-mediated $\alpha 2\beta 1$ activation," J Thromb Haem., vol. 7, pp. 1-16 (2009).
Wen et al., "Extracellular DNA is required for root tip resistance to fungal infection," Plant Physiol., vol. 151, pp. 820-829 (2009).
Whelihan et al., "Coagulation procofactor activation by factor XIa.," J Thromb Haemost., vol. 8. No. 7., pp. 1-18 PMID: 20456758 (2010).
Whelihan et al., "In vitro and in vivo characterization of a reversible synthetic heparin analog," Thromb Res., vol. 138, pp. 1-27 (Feb. 2016).
Whelihan et al., "Red blood cells and thrombin generation is sickle cell disease," Thromb. Res., vol. 133, Sippl 1, pp. 1-5 (May 2014).
Whelihan et al., "The contribution of red blood cells to thrombin generation in sickle cell disease: meizothrombin generation on sickled red blood cells," J Thromb Haemost., vol. 11, No. 12, pp. 2187-2189 (Dec. 2013).
Whelihan et al., "The Role of the Red Cell Membrane in Thrombin Generation," Thromb Res., vol. 131, No. 5, pp. 377-382, PMID:23402970 (May 2013).
Whelihan et al., "Thrombin generation and cell—dependent hypercoagulability in sickle cell disease," J Thromb Haemost., pp. 1-12 (2016) [Epub ahead of print].
Whelihan et al., "Thrombin generation and fibrin clot formation under hypothermic conditions: an in vitro evaluation of tissue factor initiated whole blood coagulation," J Crit Care, vol. 29, No. 1, pp. 1-17 (Feb. 2014).
Yousefi et al., "Catapult-like release of mitochondrial DNA by eosinophils contributes to antibacterial defense," Nat Med., vol. 14, pp. 949-953 (2008).
Yuan et al., "CIB1 is an endogenous inhibitor of agonist-induced integrin $\alpha IIb\beta 3$ activation," J Cell Biol., vol. 172, No. 2, pp. 169-175 (2006).
Yuan et al., "CIB1 is essential for mouse spermatogenesis," Mol Cell Biol., pp. 8507-8514 (2006).
Zayed et al., "Tumor growth and angiogenesis is mpaired in CIB1 knockout mice," J Angiogenesis Res., vol. 2, No. 17, pp. 1-8 (2010).
Zemljic-Harpf et al., "Cardiac-Myocyte Specific Excision of the Vinculin Gene Disrupts Cellular Junctions Causing Sudden Death or Dilated Cardiomyopathy," Mol Cell Biol, vol. 27, No. 21, pp. 7522-7537 (2007).
Zhao et al., "A novel image-based quantitative method for the characterization of NETosis," Journal of Immunological Methods, vol. 423, pp. 1-17 (2015).
Farrell et al., "A Gas DREADD mouse for selective modulation of cAMP production in striatopallidal neurons," Neuropsychopharmacology, vol. 38, No. 5, pp. 854-862 (Aug. 2013).
Fuchs et al., "Neutrophil Extracellular Trap (NET) Impact on Deep Vein Thrombosis," Arterioscler. Thromb. Vasc. Biol., vol. 32, pp. 1777-1783 (Aug. 2012).
Heineke et al., "CIB1 is a Regulator of Pathological Cardiac Hypertrophy," Nat Med., vol. 16, No. 8, pp. 872-879 (Aug. 2010).
Kessenbrock et al., "Netting neutrophils in autoimmune small-vessel vasculitis," Nature Medice, vol. 15, No. 6, pp. 623-625 (Jun. 2009).
Noubouossie et al., "In Vitro Activation of Coagulation by Human Neutrophil DNA and Histone Proteins but not Neutrophil Extracellular Traps," Blood, pp. 1-27 (Dec. 2016).
Richman et al., "Analysis of cell-cycle specific localization of the Rdi1p RhoGDI and the structural determinants required for Cdc42p membrane localization and clustering at sites of polarized growth," Curr Genet., vol. 45, No. 6, pp. 339-349 (Apr. 2004).
Simonyan et al., "Deep Inside Convolutional Networks: Visualising Image Classification Models and Saliency Maps," https://arxiv.org/abs/1312.6034, pp. 1-8 (Apr. 19, 2014).
Whelihan et al., "Prothrombin activation in blood coagulation: the erythrocyte contribution to thrombin generation," Blood, vol. 120, No. 18, pp. 1-34 (2012).
Zhang et al., "Neutrophils, Platelets, and Inflammatory Pathways at the Nexus of Sickle Cell Disease Pathophysiology," Blood, vol. 127, No. 7, pp. 1-38 (2016).

* cited by examiner

QUANTITATION OF NETOSIS USING IMAGE ANALYSIS

TECHNICAL FIELD

This specification relates generally to quantitation of NETosis (Neutrophil Extracellular Traps) and more particularly to quantitation of NETosis by computer-implemented image analysis.

BACKGROUND

NETosis (Neutrophil Extracellular Traps) is a mode of neutrophil cell death involving decondensation of chromatin and its merging with cytoplasmic granule proteins to create a net-like structure for entrapping pathogenic elements. Patients with chronic granulomatous disease (CGD) are unable to produce sufficient NETS and are therefore immune deficient. Furthermore excessive NETs contribute to complications in many inflammatory conditions such as sepsis, lupus, cancer, acute respiratory distress syndrome (ARDS) and deep vein thrombosis. NETosis proceeds by one of two major mechanisms: ROS-dependent and ROS-independent. The ROS-dependent pathway involves the activation of protein kinase C (PKC) followed by ROS production by NADPH oxidase whereas the ROS-independent one involves activation of the Ca+2-dependent enzyme PAD4.

Although extensively researched, a standardized method for a high throughput quantitative assessment of NETosis is not available despite the great need for it in view of the rapid proliferation of biological and chemical agents exhibiting poorly characterized potentials to induce NETosis and diseases that involve NETosis.

SUMMARY

This specification describes methods and systems for characterization of NETosis (Neutrophil Extracellular Traps) in neutrophils. In some examples, a method includes acquiring an image of a sample of neutrophils. The method includes classifying each neutrophil depicted in the image as having either a NETotic or non-NETotic nucleus using one or more processors executing a convolutional neural network (CNN) trained on images of NETotic and non-NETotic neutrophil nuclei. The method includes generating an output indicative of a number of neutrophils classified as having a NETotic nucleus and a number of neutrophils classified as having a non-NETotic nucleus.

DESCRIPTION

Figures 1A, 1B:
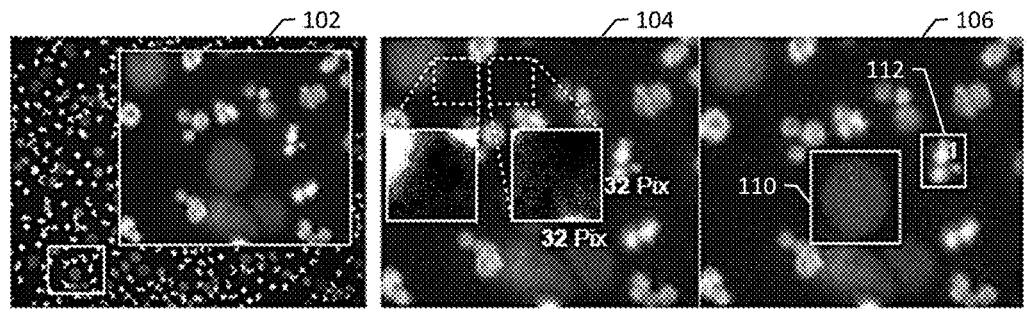
FIG. 1A shows several example image panels illustrating characterization of NETosis.
FIG. 1B shows confusion matrices that were used to assess classifier performances.

This specification describes methods and systems for characterization of NETosis (Neutrophil Extracellular Traps) in neutrophils. The methods and systems are described with respect to a study performed using example methods and systems. The examples are provided for purposes of illustration, and the claimed subject matter may be broader than the examples provided.

This specification describes an assay for the assessment of 1) the EC50 of NETotic agonists in adherent human neutrophils and 2) the NETosis mechanism specific to these agonists. Neutrophils were isolated from peripheral blood of healthy volunteers and allowed to adhere to 96-well plates before stimulation with different concentrations of agonists. We established our assay with two widely used agonists, PMA, a PKC activator and A23187, a Ca+2 ionophore. NETosis data were acquired using the automated BD Pathway 855 Bio-imaging Systems. An image processing algorithm was created to distinguish two populations related to neutrophil nuclear size, intensity and texture. Our assay is the first to describe a semi-automated imaging and analysis method for the study of NETosis and is a positive step towards standardizing the quantitation of NETosis in isolated cells. This assay has potential applications in screening novel pharmaceuticals and in analyzing cells from patients with various diseases.

We have generated an efficient pipeline from primary human neutrophil isolation to quantitative NETosis analysis by combining high-throughput imaging with deep machine learning for image analysis, eliminating the need for manual annotation, prior domain knowledge or use of biological markers. Two convolutional neural network (CNNs) architectures achieved 94% or 99% accuracy respectively in quantitating the percentage of NETotic cells imaged using high content microscopy. Saliency maps were generated to determine how the network is able to discriminate the two nuclear phenotypes by assessing pixels' importance to object identification. The applicability of the current method was tested using neutrophils from healthy individuals and patients with sickle cell disease (SCD). We show for the first time that SCD patients harbor neutrophils that are insensitive to one NETotic pathway (ROS-dependent) but respond normally to the other (PADIV-dependent), which could impact their innate immune response.

Cell image classification is a laborious task that has traditionally been relegated to heavily supervised image analysis tools that depend on continuous user input, such as those built into image acquisition software. However, the reduced error rate and superhuman learning speed of semi- or un-supervised machine learning tools is transforming this field. We demonstrate the feasibility of training two different CNNs to classify human neutrophil nuclei undergoing NETosis.

NETosis is a cell response to various signals and is phenotypically characterized by nuclear swelling due to chromatin de-condensation followed by release into extracellular space[1]. Although excessive NETosis is detrimental to an organism[2]; it is a vital part of the innate immune system that has been conserved by evolution in multiple animal species[3]. To date two different NETosis mechanisms have been identified: the peptidyl arginine deiminase (PADIV)- and the ROS-dependent pathways[4,5]. Also identified is a vesicular mechanism of extruding nuclear DNA, which is thought to be rapid, precede nuclear swelling and rupture, and to occur in vivo[6]. While different signaling pathways characterize each of the three mechanisms, a common biomarker has yet to be identified[7]. However, one defining characteristic of NETotic cells is the discernible change in nuclear shape (from segmented to spherical/ovoid) due to chromatin decondensation. Early attempts at quantifying of NETosis capitalized on the nuclear shape change by using the Heywood circularity factor where a value approaching 1.0 marks a NETotic nucleus[8]. Furthermore, the aforementioned analysis is dependent on performing experiments from start to finish on unfixed, live neutrophils, as the dye used to detect neutrophils undergoing NETosis cannot penetrate cells with an intact plasma membrane. This is a challenge given that neutrophils can only survive for a short time in culture following isolation. Conventional NETosis detection relies on assessing the activity of neutrophil elastase (NE) that is bound to DNA. This method would certainly detect ROS-dependent NETosis but not PADIV-dependent as there is no evidence that NE is involved in chromatin decondensation by the latter mechanism.

In the present study we introduce a new approach to the quantification and study of NETosis based on nuclear morphological changes observed after cell fixation, eliminating the urgency of performing experiments on live cells. Additionally, both image acquisition and analysis are performed on thousands of nuclei adhered to 96-well plates approaching high-throughput capacity. Image analysis and quantitation were performed using convolutional neural networks (CNNs), a machine learning paradigm currently upending the technologies of image, voice and pattern recognition. CNNs were inspired by the structure of the mammalian visual cortex in its ability to learn patterns and features and to compute complex object semantics. Indeed a recent systematic analysis of CNNs' resemblance to the temporal and spatial brain representation of real-world objects revealed a surprising similarity in architecture as well as stages of cortical image processing[9].

Human-annotated microscope images were used to train and test two deep CNNs in classifying NETotic (class 2) and non-NETotic (class 1) fluorescently-labeled individual nuclei. The CNNs use two training approaches: pixel-level (PL) end-to-end training and object-level (OL) classification techniques. PL is a CNN of simple architecture, so we were able to train and deploy it on commodity hardware, whereas OL utilized high performance computing in this example due to its deep architecture. In addition, class 0 for PL denotes randomly selected pixels lacking a signal (blank areas); whereas for OL class 0 denotes all objects not classified as 1 or 2 which may contain areas of spread NETs or nuclei not identifiable as one of the two classes. The dataset was divided into a training/validation set (80%, corresponding to a total of approximately 83,000 annotated nuclei) to train the classifier and a 20% out-of-sample nuclei for holdout evaluation. PL and OL yield 98.9% and 94.2% accuracy, respectively, assessed using confusion matrices (FIG. 1B) in classifying NETotic and non-NETotic nuclei signifying successfully learned phenotype classifications. The slightly lower accuracy score of OL is a consequence of the more demanding discrimination task that the model is trained to perform. In addition, both PL and OL performed similarly in a quantitation task by predicting the total number of NETotic and non-NETotic nuclei in images containing several hundred nuclei per image (FIG. 1C). The outstanding performance of OL compared to PL is due to the law of large numbers since the classification events are nearly independent random variables of which there are usually hundreds of samples per image. The truly extraordinary performance of OL ($R^2=0.99$) can also be attributed to the extremely deep network and the world-class training used as a starting point for our study.

Figure 3A:
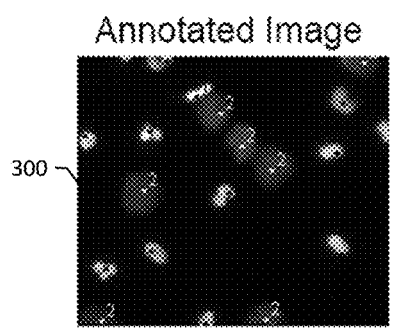
FIG. 3A illustrates a representative section of an image with numerical annotations for type 1 (non-NETotic) and 2 (NETotic)
Figure 3B:
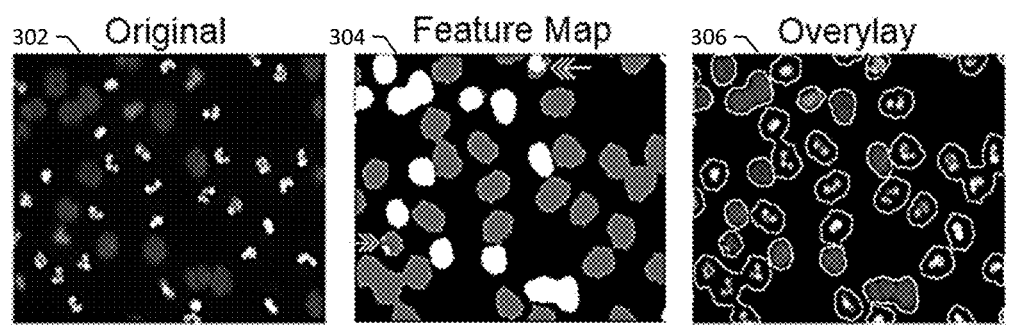
FIG. 3B shows, for PL CNNs, an original image and a probability feature map and an overlay image.
Figure 3C:
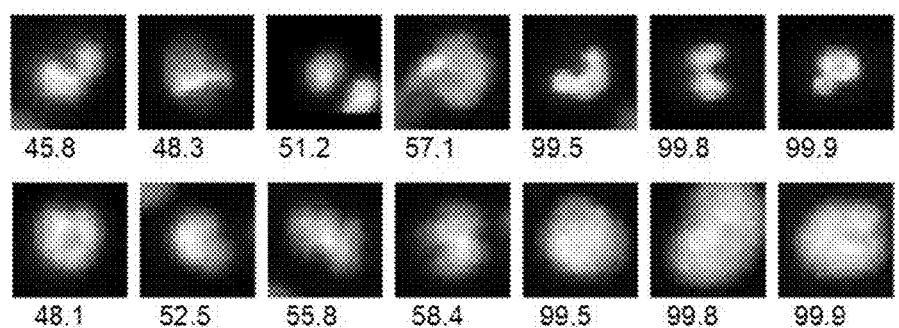
FIGS. 3C and 3D show Guided_Grad_Cam saliency maps of several non-NETotic and NETotic nuclei.
Figure 3D:
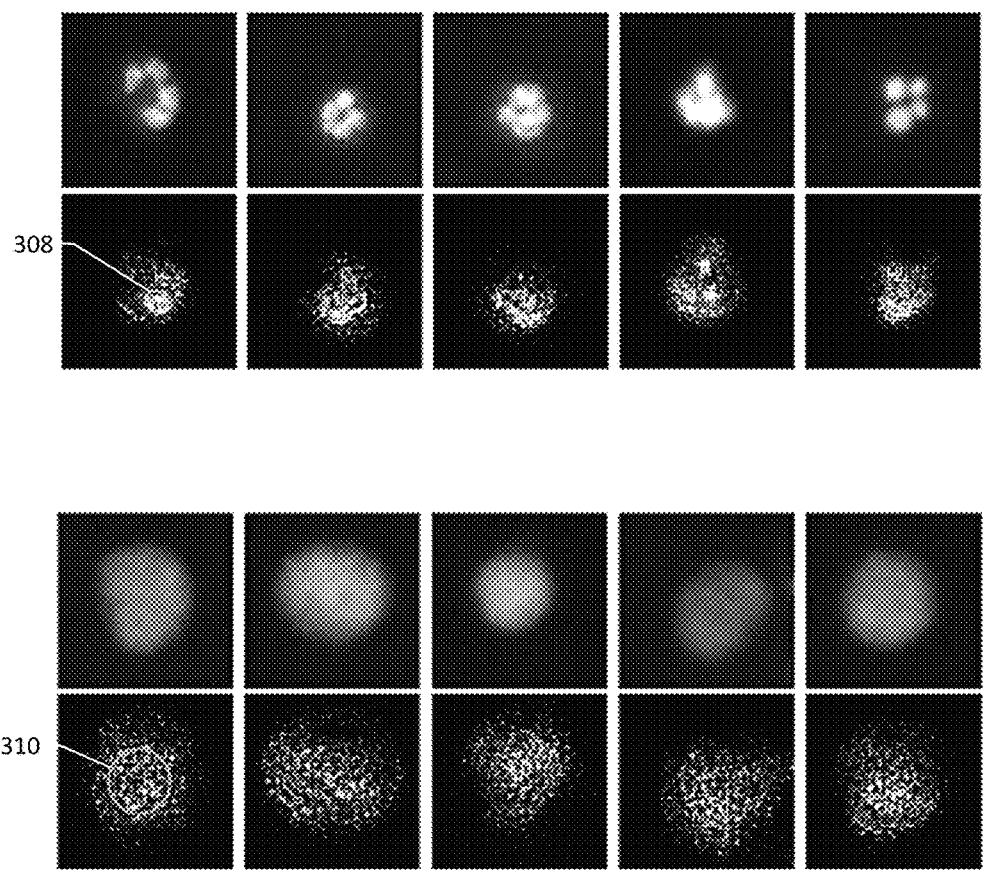

We obtained examples of images with low and high network output activation to gain insight into the models' understanding of the data (e.g., as shown in FIG. 3C). Additionally, a class saliency map was computed by analyzing the gradient of output class in relation to input image, essentially determining which pixels/regions in the input image most influence the networks' decision[10]. Saliency maps were generated from 10 representative NETotic and 10 non-NETotic single nuclei (an example of each type are shown in FIG. 1D, additional examples are shown in FIG. 3D). Saliency maps of non-NETotic (class 1) nuclei show two or several closely clustered pixel groups that strongly resemble the original input image whereas NETotic nuclei maps have a more dispersed pixel distribution with slight emphasis on a relatively central region in the nucleus. This central region in NETotic nuclei could represent the inner most core of the chromatin that has not been completely de-condensed or an alternative region with potential biological significance that has not be identified.

Reports of CNNs out-performing humans in feature recognition provided an impetus to investigate whether a third CNN classifier can differentiate between NETotic nuclei resulting from PADIV or ROS pathways, given the substantial divergence in the molecular mechanisms mediating each. In addition, the high specificity of some NETosis agonists for activation of only one of these pathways provided an essential tool to address this question (e.g., as shown in FIG. 3E). The CNN was able to differentiate with 73% accuracy the two type of NETotic nuclei that to a human eye are indistinguishable (FIG. 1E, images to the right of plot).

The CNN classifier was used to address open quantitative questions such as 1) the concentration-response relationship with commonly used NETosis agonists and 2) the concentration-response of neutrophils isolated from patients with a condition associated with altered NETosis response. Using A23187 (Calcimycin) to activate the PADIV-dependent and PMA to activate the ROS-dependent pathways, we determined the EC50 values (concentrations they induced 50% of neutrophils to undergo NETosis) to be 0.9 µM, and 2.1 nM respectively.

The availability of EC50 allows for a more reliable assessment of the potency of emerging NETosis inhibitors as well as the potency of newly discovered NETosis agonists. Because the third CNN allows our methodology to discriminate PADIV-dependent versus independent NETotic pathways (FIG. 1E), one can more readily assign signaling mechanisms to novel agonists. We observed nuclei with unusual shapes that resembled neither normal nor NETotic nuclei, suggesting intermediary stages of NETosis that could be potentially segregated into subclasses of NETosis using additional training of our classifiers. Using coefficient of variance (% CV), we determined that inter-assay variability was 31%±6 (mean±SD) given that each assay represents neutrophils from a different donor; whereas intra-assay variability was ≤20%±10.

We next applied this assay to an inflammatory disease that has been suspected of being influenced by NETosis; patients with sickle cell disease (SCD) suffer chronic inflammation due to recurrent ischemia/reperfusion injuries and are hypercoagulable. The hypercoagulability is thought to be due to at least in part to circulating NETs similar to other inflammatory diseases. Soluble components presumably from NETs (DNA and nucleosomes) are detectible in plasma from both SCD patients and humanized SCD mice[11, 12]. Furthermore, neutrophils from healthy individuals exposed to plasma from SCD patients causes NET generation. Because SCD neutrophils function at a reduced capacity for oxidative burst and produce less ROS than non-SCD neutrophils, we asked whether the ROS-dependent NETosis pathway is affected[13-15]. Only patients at steady-state were included in the study. SCD neutrophils and neutrophils from non-SCD donors responded similarly to A23187; however, SCD neutrophils were comparatively insensitive to PMA (FIG. 2D-E), which requires ROS to mediate NETosis. Reduction of neutrophils' oxidative burst capacity also occurs in conditions such as chronic granulomatous disease (CGD), and results in reduced NETosis[16]. The divergence of our results from those previously published are possibly due to our observation of NETosis in neutrophils directly without the use of a surrogate NETosis biomarker.

Our described method offers a major improvement over manual annotation and automated but fully-supervised image analysis in NETosis research. We have trained and implemented two classification models to differentiate NETotic and non-NETotic human neutrophils using distinct morphological features of the nucleus. The models performed similarly with the given volume of annotated data; however, in many cases such volumes may not be attainable and a possible solution is data augmentation using input image manipulation[17]. Furthermore, although the current analysis was limited to fixed cells to the exclusion of the more morphologically complex spread NETs, this analysis could be applied to live cell imaging which is likely to be more informative. Moreover, the tools we used can be modified to accommodate the need for morphological studies of various cell types and subcellular structures.

Figure 1C:
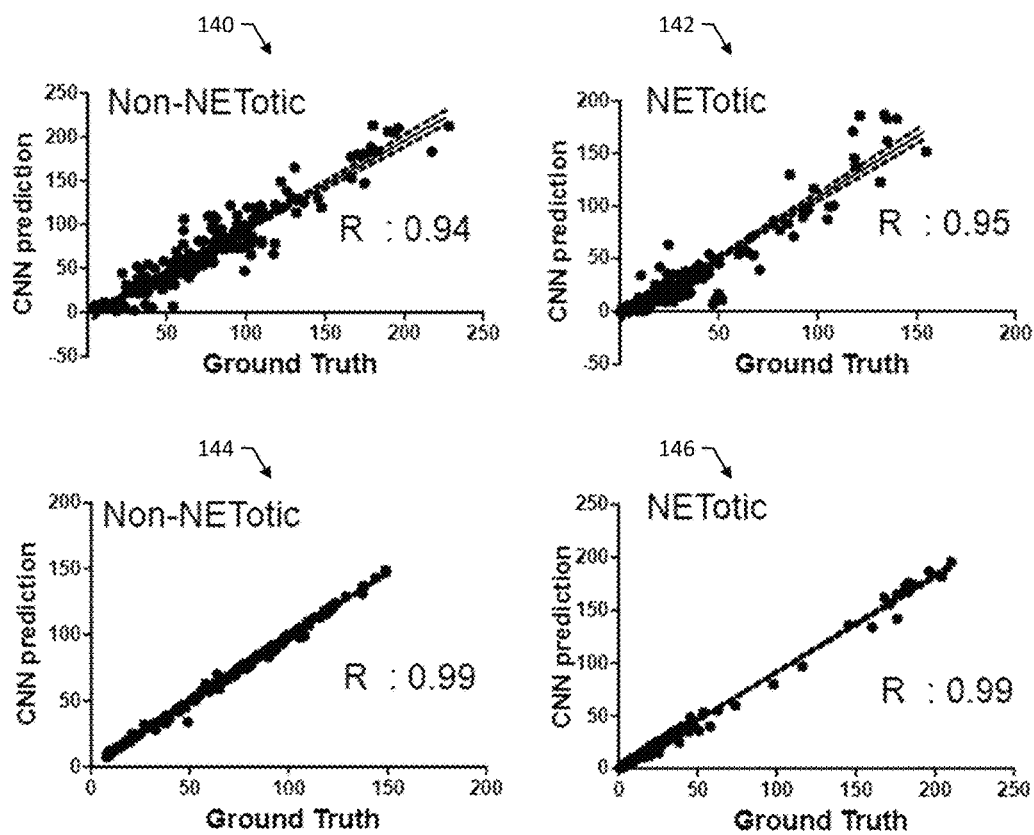
FIG. 1C shows two graphs for pixel-level CNN classification.
Figure 1D:
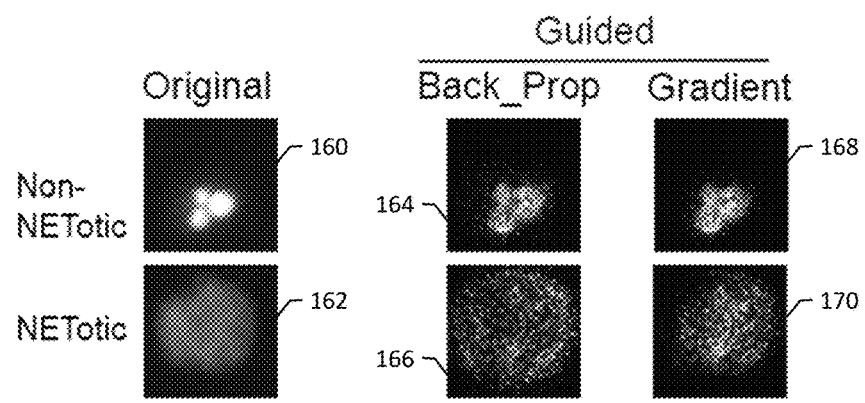
FIG. 1D shows example image panels for assessing relative contributions of individual pixels to the trained CNN's classification decision.
Figure 1E:
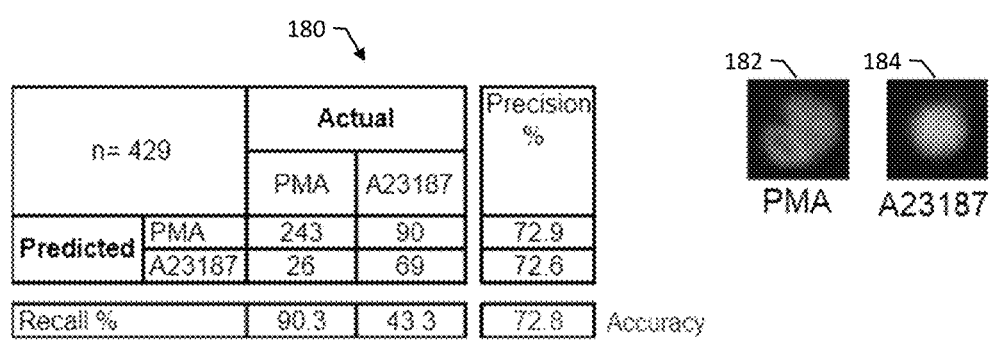
FIG. 1E shows a confusion matrix for assessing the performance of a classifier CNN trained to discriminate between NETotic nuclei that appear similar to the human eye.

FIG. 1A shows several example image panels illustrating characterization of NETosis. The first panel 102 represents one field (672×512 pixels of a 16-bit image) out of 36 total fields in a typical image representing approximately 16% of the well surface area and 2% of the total cells plated in a 96-well plate.

The second panel 104 illustrates pixel-level patches. The pixel-level (PL) classifier was trained by scanning the whole image (a total of 4032×3072 pixels) in 32×32 pixel patches and classifying each patch as class 1 (non-NETotic) or class 2 (NETotic). Each 32×32 pixel patch is assigned a probability value that was used to construct a feature map as shown in FIG. 3B. The third panel 106 illustrates object-level image segments. For the object-level (OL) classifier, bounding boxes of variable dimension are drawn around all objects identified in the image using segmentation by iterative erosion and dilation, resized to a 112×112 patch, and used as training data.

FIG. 1B shows confusion matrices 120 and 122 that were used to assess classifier performances. Precision is the fraction of correctly predicted nuclei out of the total number of predictions made and recall is the fraction of correctly predicted nuclei out of the total number of true positive nuclei. The accuracy numbers denote model accuracy, which is the percentage of total correct predictions by the CNN.

To assess the fidelity of the classifiers in nuclei quantitation, the total number of non-NETotic and NETotic nuclei predicted by the classifiers were compared to the ground truth or manually annotated data. FIG. 1C shows two graphs 140 and 142 for pixel-level CNN classification, including one graph 140 for non-NETotic cells and one graph 142 for NETotic cells. FIG. 1C shows two graphs 144 and 146 for object-level CNN classification, including one graph 144 for non-NETotic cells and one graph 146 for NETotic cells.

FIG. 1D shows example image panels for assessing relative contributions of individual pixels to the trained CNN's. The first two image panels show original images 160 and 162 of a non-NETotic cell and a NETotic cell. Both Guided Backpropagation (as shown in panels 164 and 166) as well as Gradient-weighted Class Activation Mapping (as shown in panels 168 and 170) were used to generate saliency maps highlighting the relative contributions of each pixel to the CNN's prediction. The brighter a pixel or a group of pixels are, the more important they are in the CNN's prediction. A surprising finding is the importance of a "triggering" central group of pixels in the NETotic nucleus that does not appear to correspond to any specific region in the original input image but that are important in the CNN's classification of a class 2. Additional saliency maps of both NETotic and non-NETotic nuclei are shown in FIG. 3D.

FIG. 1E shows a confusion matrix 180 for classifying NETotic nuclei that are a result of treatment with PMA (as illustrated in example image 182) or A23187 (as illustrated in example image 184), leading to ROS- or PADIV-dependent NETosis respectively appear very similar to the human eye and are difficult to differentiate (representative images of each shown on right of matrix). A CNN trained on a total of 1286 individual NETotic nuclei (807 nuclei from PMA treatment and 479 nuclei from A23187 treatment) was able to differentiate between them with an accuracy of 73%.

Figure 2:
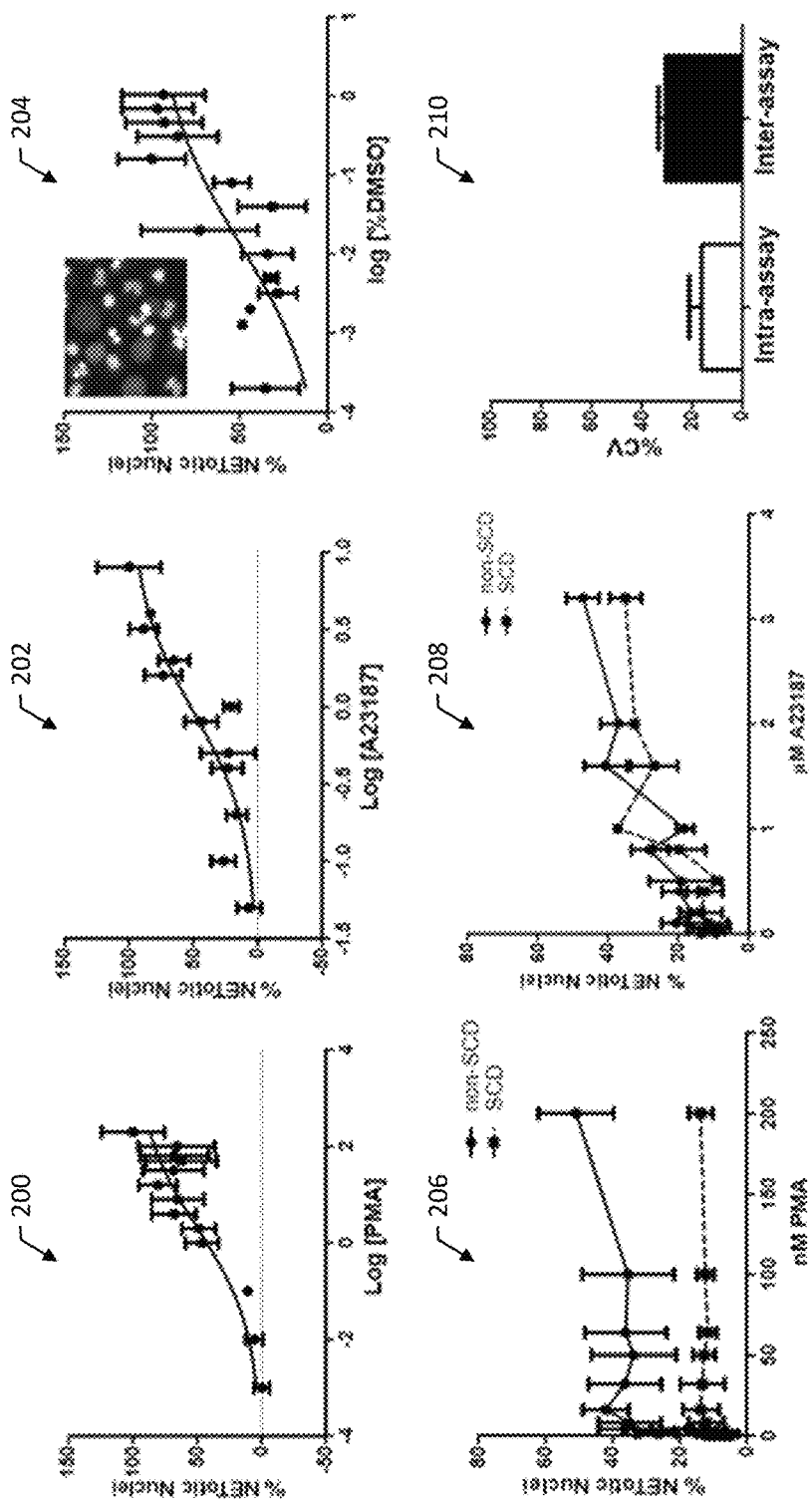
FIG. 2 shows several graphs plotting concentrations of agonists against the percentage of NETotic nuclei in a sample as determined using a trained CNN.

FIG. 2 shows several graphs plotting concentrations of agonists against the percentage of NETotic nuclei in a sample as determined using a trained CNN. Human neutrophils from healthy volunteers were treated with increasing concentrations of PMA (n=11) (as shown in graph 200) or A23187 (n=8) (as shown in graph 202) under sterile conditions to generate concentration-response curves that allowed us to calculate $EC_{50}$ values of 2.1 nM and 0.9 μM for PMA and A23187, respectively.

Adherent neutrophils were treated for 2 hours with either agonist or DMSO vehicle. DMSO treatment alone causes neutrophil NETosis reaching a maximum response of 30% with 0.16% DMSO. The resulting NETotic nuclei are visually indistinguishable from those observed with PMA- or A23187-treatments as shown graph 204. DMSO is the recommended solvent for both PMA and A23187.

The same conditions for cell isolation and treatment were used for neutrophils from SCD patients at steady-state (n=7), and the results are shown in graphs 206 and 208. Neutrophils from patients with SCD responded poorly to PMA treatment (two-way ANOVA, p<0.05) suggesting impairment in the ROS-dependent NETotic pathway; whereas little difference was observed between SCD and non-SCD with respect to A23187 treatment suggesting that NETosis via the PADIV pathway is unimpaired.

Graph 210 illustrates plate-to-plate and well-to-well variability are represented by inter-assay and intra-assay coefficient of variance (CV), respectively. Each plate represents one donor or patient.

The following sections describe further details regarding the study and the methods and systems for characterization of NETosis.

Blood Donors

Consent for SCD and non-SCD blood donors was obtained by research personnel under IRB #17-3148. Sickle Cell patients in steady state were recruited from the UNC Sickle Cell Comprehensive Program outpatient clinic. Blood samples were collected via venipuncture from healthy volunteers in the research laboratory setting or from UNC Healthcare Blood Donation Center located at UNC hospital. Blood draw was performed by experienced phlebotomists. Inclusion and exclusion criteria for both SCD and non-SCD volunteers are outlined below.

SCD
Inclusion
  Diagnosis of SCD (genotype SS, SC or Sβ0thalassemia) non-crisis at time of enrollment and no acute pain episodes in the previous 4 wks
Exclusion
  Inability to provide informed consent
  <18 years of age.
  Anticoagulation therapy
  Recent history of hemoglobin levels of <6 g/dL
  Less than 3 months have transpired since last transfusion.
  Pregnancy
Non-SCD
Inclusion
  >18 years of age.
  Healthy and of either sex
Exclusion
  Inability to provide informed consent based on the judgment of study personnel.
  <18 years of age.
  Anticoagulation therapy
  Taking Tylenol and/or Advil within 3-4 days prior to blood draw Pregnancy
  Sample Collection, Neutrophil Isolation and Treatment Approximately 5 mL of blood was collected from each donor in vacutainers coated with EDTA (BD 367863). Following collection, the blood sample was handled under sterile conditions throughout treatment with agonist and up to cell fixation. Neutrophil isolation was performed using EasySep Direct Human Neutrophil Isolation Kit from StemCell Technologies (#19666) based on neutrophil negative selection from whole blood. In brief, unwanted cells are crosslinked to magnetic particles via a tetrameric antibody complex. An average of $4.4 \times 10^7$ and $5.5 \times 10^7$ total cells can be isolated from 5 mL of blood from non-SCD and SCD donors respectively. Neutrophil isolation from SCD patients by density gradient centrifugation presents a challenge due to the altered rheology of SCD blood and the ineffectiveness of RBC sedimentation by dextran due to the low RBC aggregation index and aggregation rate of in sickle patients[1]. RBCs from SCD patients have to be eliminated by positive selection targeting a membrane surface marker such as glycophorin A.

Cells are plated at a density of $3 \times 10^6$/well in 96-well plates (Greiner Bio-One, Germany, 655986). This seeding density is optimal for allowing adequate spacing between nuclei once chromatin decondensation takes place and facilitates object identification and image analysis by CNNs. Cells are cultured in RPMI 1640 L-glutamine media (Gibco/Thermo Fisher Scientific, Grand Island, USA, 11875-093) supplemented with 0.5% FBS (Gibco/Thermo Fisher Scientific, Grand Island, USA, 10438018) for a total of 3 hours. The first hour allows the cells to adhere firmly to the well surface and 2 hours are allotted for treatment with agonists or vehicle control. Every assay condition is run in duplicates and for each well treated with a certain concentration of agonist, a neighboring well is treated with the same concentration of vehicle. Following agonist incubation, neutrophils were fixed with 4% paraformaldehyde for 20 min before staining.

Cell Staining and Imaging

The nucleic acid stain SYTOX Green (Invitrogen/Molecular Probes, Oregon, USA, S7020) is used at a concentration of 0.05 µM to visualize the nucleus. The BD Pathway imaging system was used to obtain 36 total consecutive images/well. Images are stitched together by the AttoVision acquisition software to yield one image representing approximately 16% of the total surface area of the well in a 96-well plate.

Image Analysis

A total of 103,874 individual nuclei were manually annotated using ImageJ. Approximately 80% of the annotated dataset was used to train the CNN classifiers. Annotated nuclei were designated as type 1 or non-NETotic if clear nuclear segmentation is present whereas type 2 or NETotic nuclei were distinguished based on lack of clear nuclear segmentation and diffuse SYTOX Green stain. Spread NETs or nuclei that could not be identified as belonging to either of the two classes were labeled as the negative class for OL. A screenshot of a representative annotated image is shown in FIG. 3A. A 20% holdout set served to test the classifier performance as outlined in the confusion matrices in FIG. 1B.

PL CNN Analysis

The Pixel-Level (PL) Convolutional Neural Network (CNN) analysis proceeded in two stages.

Stage 1. Cell Recognition/Discrimination Training.

Data Preprocessing: First, patches of each 512×672 image indicating NETotic, non-NETotic, or negative class (neither phenotype) were extracted by centering a 32×32 box at each annotation mark (for the positive classes) and a random 32×32 box not containing an annotation mark (for the negative class). The result was 28865 negative class images and 75009 positive class images, for a total of 103874 images, which were then split evenly into 80%/20% into training and testing (hold-out) data.

Network Description: The proposed network used an architecture inspired by VGGNet, although substantially shallower to allow for training on commodity laptop hardware and to limit model complexity. There were four convolutional layers (64 filters, each 3×3), with 2×2 max-pooling and 25% dropout used between the second and third layers. The last convolutional layer was followed by a 256-node fully connected layer, and finally by a 3-node fully connected layer to indicate the three class probabilities. All activation functions were rectified linear ("ReLU") except for the last layer, which was softmax. Weights were initialized randomly before training.

Training: The training dataset did not use augmentation, and categorical cross-entropy was used as the loss function. The network was trained with a learning rate of 0.001, a decay of 1e-7, and a momentum of 0.9.

Stage 2. Training for Cell Quantitation.

Data Preprocessing: The original, unannotated images (training and testing) were then processed by applying the network trained in Stage 1 to every 32×32 patch of the image, which generated 480×640×3 feature maps: 740 for training and 186 for testing. The feature maps generated were associated with counts by phenotype from the original annotations.

Network Description: The proposed network again used an architecture inspired by VGGNet, but even shallower than in Stage 1 in order to limit model complexity because of the small training set size. There were two convolutional layers (32 filters, each 3×3), with 2×2 average-pooling used between them and 2×2 max-pooling used after them. This was followed by a 256-node fully connected layer, and finally by a 2-node fully connected layer to indicate the two object counts. All activation functions were rectified linear ("ReLU").

Training: Mean absolute error was used as the loss function. The network was trained with a learning rate of 0.001, a decay of 1e-7, and a momentum of 0.9. The network was trained for 30 epochs.

Overall Testing.

The 186 feature maps generated from test data in Stage 2 of the preceding process were processed by the cell quantitation CNN generated in Stage 2, and the estimated counts compared to the ground-truth counts from annotation.

OL CNN Analysis

The pipeline included preprocessing both annotations and images, and training the proposed network to classify the extracted patches of the cells.

Dataset Preprocessing: Several image processing operations: repeated erosion and dilation operations remove existing noise and clarify the boundary between the cells. Afterwards, all the connected regions and their centers are detected. At this point, a 32*32 patch is utilized and the patch is labeled according to the annotation point closest to the center of the patch. The entire dataset is split into 65:15:20 ratio to create training, validation and testing datasets respectively. As part of image preprocessing, all images are normalized.

Network Description: The proposed network is inspired by DenseNet [ ], particularly its 121-layer configuration. The last layer of the DenseNet-121 is replaced by a fully connected layer with 5 hidden units in order to output 5 classes. All layers except last fully connected layer is initialized with pre-trained weights on imagenet and the last layer is randomly initialized.

Training: The training dataset is augmented by applying random rotations between −10 degrees to 10 degrees and horizontal/vertical flips in addition to original patches. Finally, each image is resized to 112*112 which is the input of the training network. The network is trained with a learning rate of 0.001 and momentum of 0.9. The learning rate is reduced by 1e-5 every 10 iterations. The network is trained until it starts to overfit, that is until the validation loss starts increasing when the training loss is decreasing.

Testing: The images are normalized and fed to the network. No data augmentation is applied in testing phase.

The Table below summarizes the breakup of the number of data points used for training/validation and testing of each model.

| | Total No. of Nuclei used for: | | |
|---|---|---|---|
| | Training | Validation | Testing |
| PL | 83099 | — | 20774 |
| OL | 65323 | 17209 | 19650 |

Phenotype Discrimination Convolutional Neural Network (CNN)

Data Preprocessing: First, 100×100 patches of each image indicating the location of a cell were extracted by manually cutting out a box around each. There were 1076 PMA-treated cell images and 638 A23187-treated cell images, both of which were then split evenly into 75%/25% training and testing (hold-out) data.

Network Description: The proposed network used an architecture inspired by VGGNet, although substantially shallower to allow for training on commodity laptop hardware and to limit model complexity. There were nine convolutional layers (64 filters, each 3×3), with 2×2 max-pooling and 25% dropout used after each three. The last convolutional layer was followed by a 256-node fully connected layer, and finally by a 2-node fully connected layer to indicate the two class probabilities. All activation functions were rectified linear ("ReLU") except for the last layer, which was softmax. Weights were initialized randomly before training.

Training: The training dataset used no augmentation, and categorical cross-entropy was used as the loss function. The network was trained with a learning rate of 0.001, a decay of 1e-7, and a momentum of 0.9. The network was trained for 100 epochs.

Testing: The 428 test images were processed by the trained CNN, and the class probabilities were thresholded at 50% to construct a confusion matrix.

Saliency Maps

We generated saliency maps for visualizing the internal "thought process" of a CNN. Saliency maps attempt to assign to each pixel of an input image some measure of how much influence on the final classification decision that pixel had, thus highlighting regions of the image which were important in the decision-making process. We used two such methods: "Guided Backpropagation Class Activation Mapping" ("Guided Backprop") and "Guided Gradient-weighted Class Activation Mapping" ("Guided Grad-CAM"). The former identifies pixels which were highly influential for the final classification probability by tracing derivatives of node activations backwards through the network from the positive class node while discarding negative influences (i.e., derivatives). The latter adds additional information to this process by also measuring the extent to which pixels occurred in an image region with a cumulatively positive effect on the final classification probability.

FIG. 3A illustrates a representative section of an image 300 with numerical annotations for type 1 (non-NETotic) and 2 (NETotic). FIG. 3B shows, for PL CNNs, an original image 302 and a probability feature map 304 that identifies the coordinates of each class in an image and precedes any quantitation task. The feature map 304 shows a probability for each of the 32×32 pixel windows analyzed in an image. Darker and lighter overlay colors denote high probability that PL has determined that a particular pixel group is a type 1 or 2 respectively. The arrows highlight two examples of nuclei with regions classified as type 1 as well as type 2. PL's confusion in the top example can be attributed to an edge effect and is the reason for our decision to disregard any nuclei positioned on the edges. The second arrow highlights a nucleus that is presenting mostly as a type 1 for the exception of two small regions on the periphery. The third panel 306 represents an overlay of the feature map on the original image.

FIGS. 3C and 3D show Guided_Grad_Cam saliency maps of several non-NETotic and NETotic nuclei that show one or more closely clustered pixels located at the periphery of the nucleus (circle 308) that the network deemed essential to the identification of this class. For NETotic nuclei, a wider distribution of pixels in the center of the nucleus (circle 310) appear to be most essential to identification.

Figure 4:
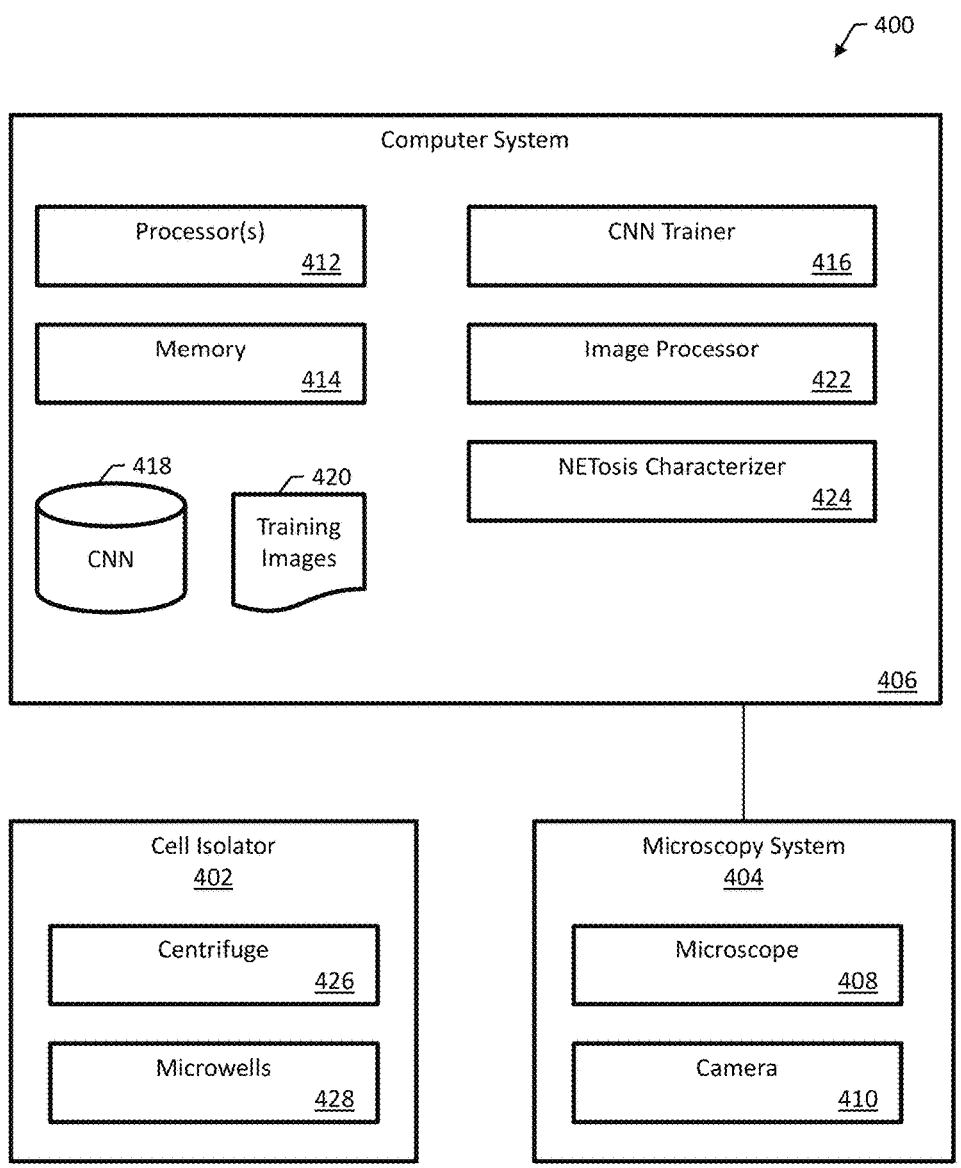
FIG. 4 is a block diagram of a system for characterization of NETosis.

FIG. 4 is a block diagram of a system 400 for characterization of NETosis. The system 400 includes a cell isolator 402 configured for isolating a sample of neutrophils from a blood sample. The system 400 also includes a microscopy system 404 and a computer system 406 programmed for receiving images from the microscopy system 404.

The microscopy system 404 includes at least a microscope 408 and a camera 410 for capturing images through the microscope 408. The microscopy system 404 can also include other components for imaging biological samples such as illumination sources and motor-controlled movement stages. For example, the microscopy system 404 can be a fluorescence imaging system for imaging microwells arranged in a sample plate. In cases where the microscopy system 404 includes a motor-controlled movement stage, the computer system 406 can be programmed to control the movement of the stage to capture an image of each microwell in a sample plate. The cell isolator 402 can include, e.g., a centrifuge 426 a sample plate including a number of microwells 428 for receiving isolating neutrophil cells.

The computer system 406 includes at least one processor 412 and memory 414 storing executable instructions for the processor 412. The computer system 406 includes a CNN trainer 416, implemented using the processor 412 and memory 414, and configured to train a CNN 418 using training images 420. The computer system also includes an image processor 422, implemented using the processor and memory 414, and configured for performing any image processing associated with training the CNN 418 or with characterizing NETosis using the CNN 418. For example, the image processor 422 can be configured for stitching together images acquired from the microscopy system 404, or for performing segmentation to segment acquired images into segments depicting individual cells, or both.

The computer system 406 includes a NETosis characterizer 424, implemented using the processor 412 and memory 414, and configured for characterizing NETosis in neutrophils using the CNN 418. The NETosis characterizer 424 is configured for acquiring an image from the microscopy system 404 and classifying each neutrophil cell depicted in the image as having either a NETotic or non-NETotic nucleus using the CNN 418. In some examples, the NETosis characterizer 424 performs pixel-level classification using a first CNN for classifying individual pixels in the image and a second CNN for counting the number of cells based on the classified pixels. In some examples, the NETosis characterizer 424 performs object-level classification by segmenting the image and classifying each segment.

The NETosis characterizer 424 generates an output indicative of a number of neutrophils classified as having a NETotic nucleus and a number of neutrophil cells classified as having a non-NETotic nucleus. For example, the NETosis characterizer 424 can display values in a graphical user interface on a display device, or save values to a file system or transmit values over a data communications network.

Figure 5:
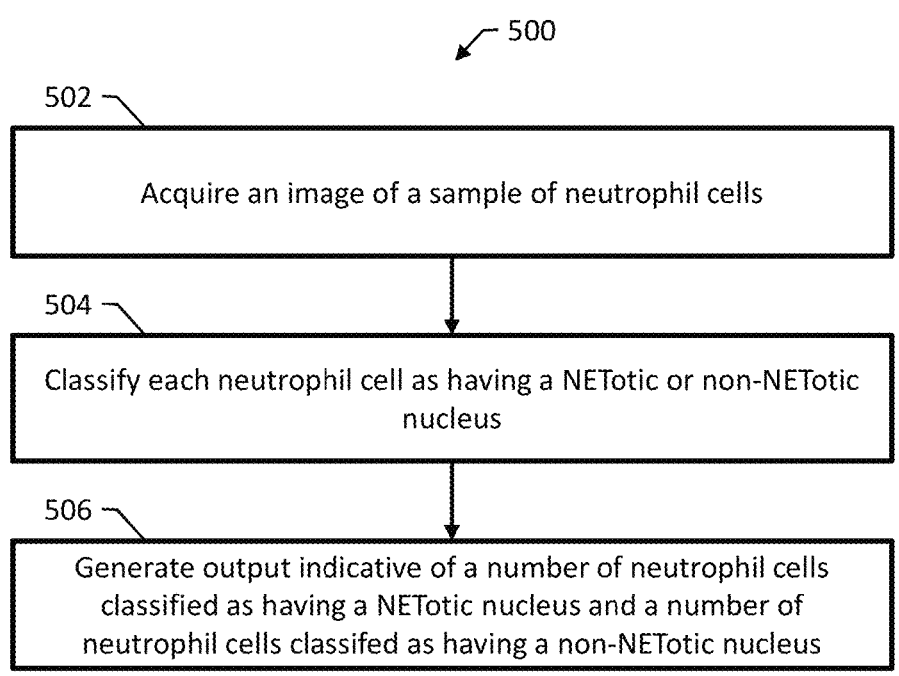
FIG. 5 is a flow chart of an example method for characterization of NETosis.

FIG. 5 is a flow chart of an example method 500 for characterization of NETosis. The method 500 can be performed, e.g., by the NETosis characterizer 424 of FIG. 4. The method 500 includes acquiring an image of the sample of neutrophils (502). The method 500 includes classifying each neutrophil cell depicted in the image as having either a NETotic or non-NETotic nucleus using a trained CNN (504). The method 500 includes generating an output indicative of a number of neutrophil cells classified as having a NETotic nucleus and a number of neutrophils classified as having a non-NETotic nucleus (506).

Although specific examples and features have been described above, these examples and features are not intended to limit the scope of the present disclosure, even where only a single example is described with respect to a particular feature. Examples of features provided in the disclosure are intended to be illustrative rather than restrictive unless stated otherwise. The above description is intended to cover such alternatives, modifications, and equivalents as would be apparent to a person skilled in the art having the benefit of this disclosure.

The scope of the present disclosure includes any feature or combination of features disclosed in this specification (either explicitly or implicitly), or any generalization of features disclosed, whether or not such features or generalizations mitigate any or all of the problems described in this specification. Accordingly, new claims may be formulated during prosecution of this application (or an application claiming priority to this application) to any such combination of features. In particular, with reference to the appended claims, features from dependent claims may be combined with those of the independent claims and features from respective independent claims may be combined in any appropriate manner and not merely in the specific combinations enumerated in the appended claims.

REFERENCES

Each of the following references is hereby incorporated by reference in its entirety.
1. Brinkmann, V. et al. Neutrophil extracellular traps kill bacteria. *Science* 303, 1532-1535 (2004).
2. Pillai, P. S. et al. Mx1 reveals innate pathways to antiviral resistance and lethal influenza disease. *Science* 352, 463-466 (2016).
3. Fuchs, T. A. et al. Novel cell death program leads to neutrophil extracellular traps. *J Cell Biol* 176, 231-241 (2007).
4. Wang, Y. et al. Histone hypercitrullination mediates chromatin decondensation and neutrophil extracellular trap formation. *J Cell Biol* 184, 205-213 (2009).
5. Papayannopoulos, V., Metzler, K. D., Hakkim, A. & Zychlinsky, A. Neutrophil elastase and myeloperoxidase regulate the formation of neutrophil extracellular traps. *J Cell Biol* 191, 677-691 (2010).
6. Pilsczek, F. H. et al. A novel mechanism of rapid nuclear neutrophil extracellular trap formation in response to *Staphylococcus aureus*. *J Immunol* 185, 7413-7425 (2010).
7. Neeli, I. & Radic, M. Opposition between PKC isoforms regulates histone deimination and neutrophil extracellular chromatin release. *Front Immunol* 4, 38 (2013).
8. Hakkim, A. et al. Activation of the Raf-MEK-ERK pathway is required for neutrophil extracellular trap formation. *Nat Chem Biol* 7, 75-77 (2011).
9. Cichy, R. M., Khosla, A., Pantazis, D., Torralba, A. & Oliva, A. Comparison of deep neural networks to spatio-temporal cortical dynamics of human visual object recognition reveals hierarchical correspondence. *Sci Rep* 6, 27755 (2016).
10. Karen Simonyan, A. V., Andrew Zisserman in arXiv (arxiv.org/abs/1312.6034; 2014).
11. Chen, G. et al. Heme-induced neutrophil extracellular traps contribute to the pathogenesis of sickle cell disease. *Blood* 123, 3818-3827 (2014).
12. Bennewitz, M. F. et al. Lung vaso-occlusion in sickle cell disease mediated by arteriolar neutrophil-platelet microemboli. *JCI Insight* 2, e89761 (2017).

13. Evans, C. et al. Impairment of neutrophil oxidative burst in children with sickle cell disease is associated with heme oxygenase-1. *Haematologica* 100, 1508-1516 (2015).
14. Qari, M. H. & Zaki, W. A. Flow cytometric assessment of leukocyte function in sickle cell anemia. *Hemoglobin* 35, 367-381 (2011).
15. Mollapour, E., Porter, J. B., Kaczmarski, R., Linch, D. C. & Roberts, P. J. Raised neutrophil phospholipase A2 activity and defective priming of NADPH oxidase and phospholipase A2 in sickle cell disease. *Blood* 91, 3423-3429 (1998).
16. van der Linden, M., Westerlaken, G. H. A., van der Vlist, M., van Montfrans, J. & Meyaard, L. Differential Signalling and Kinetics of Neutrophil Extracellular Trap Release Revealed by Quantitative Live Imaging. *Sci Rep* 7, 6529 (2017).
17. Luis Perez, J. W. in arXiv, Edn. Dec. 13, 2017 (2017).

What is claimed is:

1. A method for characterization of NETosis (Neutrophil Extracellular Traps) in neutrophils, the method comprising:
    acquiring an image of a sample of neutrophils;
    classifying each neutrophil depicted in the image as having either a NETotic or non-NETotic nucleus using one or more processors executing a convolutional neural network (CNN) trained on a plurality of training images of NETotic and non-NETotic neutrophil nuclei, wherein classifying each neutrophil cell depicted in the image comprises classifying, using a first CNN, each pixel of the image as depicting either a portion of a NETotic nucleus, a portion of a non-NETotic nucleus, or background;
    generating a first output indicative of a number of neutrophils classified as having a NETotic nucleus; and
    generating a second output indicative of a number of neutrophils classified as having a non-NETotic nucleus.

2. The method of claim 1, wherein classifying each neutrophil cell depicted in the image comprises counting, using a second CNN, the number of neutrophils classified as having a NETotic nucleus based on the classifying performed using the first CNN.

3. The method of claim 1, wherein classifying each neutrophil depicted in the image comprises, for each neutrophil classified as having a NETotic nucleus, determining whether the NETotic nucleus resulted from a first or second NETosis pathway using the CNN.

4. The method of claim 3, wherein determining whether the NETotic nucleus resulted from a first or second NETosis pathway comprises determining whether the NETotic nucleus resulted from a peptidyl arginine deiminase (PAD IV) or reactive oxygen species (ROS) pathway.

5. The method of claim 1, wherein acquiring an image of a sample of neutrophils comprises isolating the sample of neutrophils from a blood sample.

6. The method of claim 1, wherein acquiring an image of a sample of neutrophils comprises plating the neutrophils into a plurality of microwells, acquiring a well image of each well, and stitching together the well images to create the image of the sample of neutrophils.

7. The method of claim 1, wherein acquiring an image of a sample of neutrophils comprises applying a nucleic acid stain to the sample of neutrophils.

8. A method for characterization of NETosis (Neutrophil Extracellular Traps) in neutrophils, the method comprising:
    acquiring an image of a sample of neutrophils;
    classifying each neutrophil depicted in the image as having either a NETotic or non-NETotic nucleus using one or more processors executing a convolutional neural network (CNN) trained on a plurality of training images of NETotic and non-NETotic neutrophil nuclei, wherein classifying each neutrophil cell depicted in the image comprises segmenting the image into a plurality of segments each depicting one of the neutrophil cells depicted in the image;
    generating a first output indicative of a number of neutrophils classified as having a NETotic nucleus; and
    generating a second output indicative of a number of neutrophils classified as having a non-NETotic nucleus.

9. The method of claim 8, wherein classifying each neutrophil depicted in the image comprises classifying each segment and counting the number of neutrophils classified as having a NETotic nucleus using the CNN.

10. The method of claim 8, wherein classifying each neutrophil depicted in the image comprises, for each neutrophil classified as having a NETotic nucleus, determining whether the NETotic nucleus resulted from a first or second NETosis pathway using the CNN.

11. The method of claim 10, wherein determining whether the NETotic nucleus resulted from a first or second NETosis pathway comprises determining whether the NETotic nucleus resulted from a peptidyl arginine deiminase (PAD IV) or reactive oxygen species (ROS) pathway.

12. A system for characterization of NETosis (Neutrophil Extracellular Traps) in neutrophils, the system comprising:
    a cell isolator configured for isolating a sample of neutrophils from a blood sample;
    a microscopy system comprising a microscope and a camera;
    a computer system coupled to the microscopy system, the computer system comprising one or more processors and memory, wherein the computer system is programmed for:
        acquiring an image of the sample of neutrophils using the microscopy system;
        classifying each neutrophil cell depicted in the image as having either a NETotic or non-NETotic nucleus using one or more processors executing a convolutional neural network (CNN) trained on a plurality of training images of NETotic and non-NETotic neutrophil nuclei;
        generating a first output indicative of a number of neutrophils classified as having a NETotic nucleus; and
        generating a second output indicative of a number of neutrophils classified as having a non-NETotic nucleus.

13. The system of claim 12, wherein classifying each neutrophil depicted in the image comprises classifying, using a first CNN, each pixel of the image as depicting either a portion of a NETotic nucleus, a portion of a non-NETotic nucleus, or background.

14. The system of claim 13, wherein classifying each neutrophil depicted in the image comprises counting, using a second CNN, the number of neutrophils classified as having a NETotic nucleus based on the classifying performed using the first CNN.

15. The system of claim 12, wherein classifying each neutrophil depicted in the image comprises segmenting the image into a plurality of segments each depicting one of the neutrophil depicted in the image.

16. The system of claim 15, wherein classifying each neutrophil depicted in the image comprises classifying each segment and counting the number of neutrophil cells classified as having a NETotic nucleus using the CNN.

17. The system of claim 12, wherein classifying each neutrophil depicted in the image comprises, for each neutrophil classified as having a NETotic nucleus, determining whether the NETotic nucleus resulted from a first or second NETosis pathway using the CNN.

18. The system of claim 17, wherein determining whether the NETotic nucleus resulted from a first or second NETosis pathway comprises determining whether the NETotic nucleus resulted from a peptidyl arginine deiminase (PADIV) or reactive oxygen species (ROS) pathway.

19. The system of claim 12, wherein isolating the sample of neutrophils comprises plating the neutrophils into a plurality of microwells, and wherein acquiring an image of a sample of neutrophils comprises acquiring a well image of each well and stitching together the well images to create the image of the sample of neutrophil cells.

20. The system of claim 12, wherein isolating the sample of neutrophils comprises applying a nucleic acid stain to the sample of neutrophils.

\* \* \* \* \*